(12) United States Patent
Steigerwald et al.

(10) Patent No.: US 9,980,927 B2
(45) Date of Patent: May 29, 2018

(54) USE OF TAPENTADOL FOR INHIBITING AND/OR TREATING DEPRESSION AND ANXIETY

(71) Applicant: Gruenenthal GmbH, Aachen (DE)

(72) Inventors: Ilona Steigerwald, Aachen (DE); Ulrich Jahnel, Remscheid (DE); Thomas Tzschentke, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days. days.

(21) Appl. No.: 15/470,385

(22) Filed: Mar. 27, 2017

(65) Prior Publication Data
US 2017/0196822 A1   Jul. 13, 2017

Related U.S. Application Data

(60) Division of application No. 14/502,552, filed on Sep. 30, 2014, which is a continuation-in-part of application No. 13/458,510, filed on Apr. 27, 2012.

(60) Provisional application No. 61/480,621, filed on Apr. 29, 2011.

(30) Foreign Application Priority Data

Apr. 29, 2011 (EP) ..................... 11003508

(51) Int. Cl.
*A61K 31/137* (2006.01)
*A61K 9/00* (2006.01)

(52) U.S. Cl.
CPC .......... *A61K 31/137* (2013.01); *A61K 9/0053* (2013.01)

(58) Field of Classification Search
CPC ............................. A61K 31/137; A61K 9/0053
See application file for complete search history.

(56) References Cited

U.S. PATENT DOCUMENTS

| | | |
|---|---|---|
| 4,612,008 A | 9/1986 | Wong et al. |
| 4,765,989 A | 8/1988 | Wong et al. |
| 4,783,337 A | 11/1988 | Wong et al. |
| 6,248,737 B1 | 6/2001 | Buschmann et al. |
| 7,868,043 B2 | 1/2011 | Yao et al. |
| 2005/0058706 A1 | 3/2005 | Bartholomaeus et al. |
| 2008/0269326 A1 | 10/2008 | Christoph et al. |
| 2009/0012180 A1 | 1/2009 | Lange et al. |
| 2009/0215809 A1 | 8/2009 | Yao et al. |
| 2009/0306050 A1 | 12/2009 | Dinan |
| 2010/0080797 A1 | 4/2010 | Yeomans et al. |
| 2010/0227921 A1 | 9/2010 | Franklin et al. |
| 2010/0280128 A1 | 11/2010 | Jahnel et al. |
| 2010/0297181 A1 | 11/2010 | Hanada et al. |
| 2010/0297229 A1 | 11/2010 | Sesha |
| 2012/0309841 A1 | 12/2012 | Schiene et al. |
| 2014/0027351 A1 | 1/2014 | Bazer-Bachi et al. |

FOREIGN PATENT DOCUMENTS

| | | |
|---|---|---|
| DE | 10 2007 012 165 A1 | 9/2008 |
| EP | 0 693 475 A1 | 1/1996 |
| EP | 1 985 292 A1 | 10/2008 |
| JP | 2009-506076 A | 2/2009 |
| JP | 2010-531296 A | 9/2010 |
| JP | 2014-503020 A | 2/2014 |
| WO | WO 2007/025286 A2 | 3/2007 |
| WO | WO 2007/128412 A1 | 11/2007 |
| WO | WO 2008/110323 A1 | 9/2008 |
| WO | WO 2008/128740 A1 | 10/2008 |
| WO | WO 2009/067703 A2 | 5/2009 |
| WO | WO 2009/082039 A1 | 7/2009 |
| WO | WO 2012/136349 A1 | 10/2012 |

OTHER PUBLICATIONS

Ali, R.A. "Management of Diabetic Neuropathy", Malaysian Journal of Medical Sciences, 2003, vol. 10, No. 2, pp. 27-30 (printed pp. 1-4).*
Vileiktye et al. "Diabetic Peripheral Neuropathy and Depressive Symptoms", Diabetes Care, 2005, vol. 28, pp. 2378-2383.*
"Palexia retard Retardtabletten", Fachinformation Rote List Service, Aug. 2010, pp. 1-5, XP002643645.
C. Rauschkolb-Loeffler et al., "Efficacy and Tolerability of Tapentadol for Relief of Moderate-to-Severe Chronic Pain Due to Osteoarthritis of the Knee", Animals of the Rheumatic Diseases, Jun. 16, 2007, p. 507, vol. 66, No. Suppl. 2, XP009101917.
William E. Evans et al., "Pharmacogenomics: Translating Functional Genomics into Rational Therapeutics", Science, Oct. 15, 1999, pp. 487-491, vol. 286.
E. A. Shipton, "The Transition from Acute to Chronic Post Surgical Pain", Anaesthesia and Intensive Care, Sep. 2011, pp. 824-836, vol. 39, No. 5.
Jørgen B. Dahl et al., "Preventive Analgesia", Current Opinion in Anesthesiology, 2011, pp. 331-338, vol. 24.
Patricia Lavand'Homme, "The Progression from Acute to Chronic Pain", Current Opinion in Anesthesiology, 2011, pp. 545-550, vol. 24.
J. P. Rathmell et al., "Do We Have the Tools to Prevent Phantom Limb Paing?", Anesthesiology, May 2011, pp. 1021-1024, vol. 114, No. 5.
W. A. Macrae, "Chronic Post-Surgical Pain: 10 Years On", British Journal of Anaesthesia, Apr. 22, 2008, pp. 77-86, vol. 101, No. 1.
Timothy J. Brennan et al, "Characterization of a Rat Model of Incisional Pain", Pain, 1996, pp. 493-501, vol. 64.
H. Kehlet et al., "Persistent Postsurgical Pain: The Path Forward through Better Design of Clinical Studies", Anesthesiology, Mar. 2010, pp. 514-515, vol. 112, No. 3.
European Search Report dated Aug. 9, 2011 (Eight (8) pages).
Marc Afilalo et al. Efficacy and Saftey of Tapentadol Extended Release Compared with Oxycodone Controlled Release for the Management of Moderate to Severe Chronic Pain Related to Osteoarthritis of the Knee: A Randomized, Double-Blind, Placebo- and Active Controlled Phase III Study:, Clinical Drug Investigation, Aug. 1, 2010, pp. 489-505, vol. 30, No. 8, XP009148168.
B. Kuperwasser et al., "337 Evaluation of Long-Term Treatment with Tapentadol Extended Release and Oxycodone Controlled Release in Patients with Chronic Low Back or Osteoarthritis Pain: Results from Patient and Physician Global Assessments and the Euroqol 5 Dimension Questionnaire", Osteoarthritis and Cartilage, Sep. 1, 2009, p. S179, vol. 17, Supplement 1, XP026582221.

(Continued)

*Primary Examiner* — Kendra D Carter
(74) *Attorney, Agent, or Firm* — Crowell & Moring LLP

(57) ABSTRACT

The use of tapentadol (i) in the treatment of pain in a subject suffering from depression and/or from anxiety, and/or (ii) in the treatment or the inhibition of depression or anxiety.

13 Claims, No Drawings

(56) References Cited

OTHER PUBLICATIONS

B. Kuperwasser et al., "337 Health Status of Patients Who Received Tapentadol Prolonged Release During an Open-Label Extension Study", Osteoarthritis and Cartilage, Oct. 1, 2010, p. S149, vol. 18, XP027316893.

Sherwyn Schwartz et al., "Safety and efficacy of Tapentadol ER in Patients with Painful Diabetic Peripheral Neuropathy: Results of a Randomized-Withdrawal, Placebo-Controlled Trial", Current Medical Research & Opinion, Jan. 2011, pp. 151-162, vol. 27, No. 1, XP009150479.

European Search Report dated Jul. 28, 2011 (Eight (8) pages).

Ali, R.A., "Management of Diabetic Neuropathy," Malaysian Journal of Medical Sciences, 2003, vol. 10, No. 2, pp. 27-30.

Vileiktye et al., "Diabetic Peripheral Neuropathy and Depressive Symptoms," Diabetes Care, 2005, vol. 28, pp. 2378-2383.

Tzschentke et al., "(−)-(1R,2R)-3-(3-Dimethylamino-1-ethyl-2-methyl-propyl)-phenol Hydrochloride (Tapentadol HCl): a Novel μ-Opioid Receptor Agonist/Norepinephrine Reuptake Inhibitor with Broad-Spectrum Analgesic Properties", The Journal of Pharmacology and Experimental Therapeutics, 2007, pp. 265-276, vol. 323, No. 1, Departments of Pharmacology and Molecular Pharmacology and Preclinical Drug Development.

Perkins et al., "Chronic Pain as an Outcome of Surgery: A Review of Predictive Factors", Anesthesiology, Oct. 2000, pp. 1123-1133, vol. 93, No. 4, American Society of Anesthesiologists, Inc.

Joseph V. Pergolizzi Jr. et al., "Treating Acute Pain in Light of the Chronification of Pain", Pain Management Nursing, vol. 15, No. 1, Mar. 2014, pp. 380-390.

Pergolizzi et al., "Treating Acute Pain in Light of the Chronification of Pain", Pain Management Nursing, 2012, pp. 1-11.

Vadivelu et al., "Recent Advances in Postoperative Pain Management", Yale Journal of Biology and Medicine (83), 2010, pp. 11-25.

Kress, "Tapentadol and its two mechanisms of action: Is there a new pharmacological class of centrally-acting analgesics on the horizon?" European Journal of Pain, 2010, pp. 781-783, vol. 14.

Latremoliere et al., "Differential Implication of Proinflammatory Cytokine Interleukin-6 in the Development of Cephalic versus Extracephalic Neuropathic Pain in Rats", The Journal of Neuroscience 28(34), Aug. 20, 2008, pp. 8489-8501.

Ravin, L. PhD., "Preformulation", Remington Chapter 76, pp. 1409-1423, 1985 (fifteen (15) sheets).

Disanto, A., "Bioavailability and Bioequivalency Testing", Remington Chapter 77, pp. 1424-1431, 1985 (eight (8) sheets).

Knevel, A. PhD., "Separation", Remington Chapter 78, pp. 1432-1442, 1985 (eleven (11) sheets).

Phillips, G Briggs, PhD., "Sterilization", Remington Chapter 79, pp. 1443-1454, 1985 (twelve (12) sheets).

Siegel, F. PhD., "Tonicity, Osmoticity, Osmolality and Osmolarity", Remington Chapter 80, pp. 1455-1472, 1985 (eighteen (18) sheets).

Giles et al., "Plastic Packaging Materials", Remington Chapter 81, pp. 1473-1477, 1985 (five (5) sheets).

Sclarra et al., "Aerosols", Remington Chapter 93 , pp. 1662-1677, 1985 (sixteen (16) sheets).

Anonymous, "Palexia® retard Retardtabletten", 2010, pp. 1-5, XP-002643645.

English translation (Jpn J Psychosom Med, 2010, pp. 1045-1050, vol. 50, No. 11, Presented by Medical Online, with English abstract).

English translation (The Japanese Journal of Clinical and Experimental Medicine, 2001, pp. 91-94.).

English translation (Masuda, The Journal of Japanese Society for the Study of Chronic Pain, 2006, pp. 23-27, vol. 25, No. 1, Presented by Medical Online, Department of Anesthesiology, Showa University School of Medicine, with English abstract).

Emanuel et al., "Euthanasia and physician-assisted suicide: attitudes and experiences of oncology patients, oncologists, and the public", The Lancet, Jun. 29, 1996, pp. 1805-1810, vol. 347.

Magni et al., "Suicidality in chronic abdominal pain: an analysis of the Hispanic Health and Nutrition Examination Survey (HHANES)", International Association for the Study of Pain, Feb. 3, 1998, pp. 137-144.

Smith, "The Epidemiology and Treatment of Depression When It Coexists with Somatoform Disorders, Somatization, or Pain", 1992, pp. 265-272, Elsevier Science Publishing Co., Inc., New York, NY.

Nossaman et al., "Advances in Perioperative Pain Management: Use of Medications with Dual Analgesic Mechanisms, Tramadol & Tapentadol", Anesthesiology Clin 28, 2010, pp. 647-666.

Third Party Observation for Application No. EP 20120718064 dated Jul. 7, 2016 (Four (4) pages).

The U.S. Food and Drug Administration approved NUCYNTA (Tapentadol) Medication Guide, revised Jun. 2010, PriCara, Division of Ortho-McNeil-Janssen Pharmaceuticals, Inc., Reference ID: 2858116, 26 pages.

Wild, J.E., et al., "Long-term safety and tolerability of tapentadol extended release for the management of chronic low back pain or osteoarthritis pain", Abstract, Pain Pract. Sep.-Oct. 2010; 10(5), Jul. 7, 2016, two pages.

Third Party Observation for Application No. EP 20120718065 dated Jul. 12, 2016, four pages.

Grudt et al., "mu-Opioid agonists inhibit spinal trigeminal substantia gelatinosa neurons in guinea pig and rat", Journal of Neuroscience, Mar. 14, 1994, Abstract, two pages.

Palexia Filmtabletten, Gruenenthal, Aug. 19, 2010, 13 pages.

Williamson et al., "Role of opioid receptors in neurogenic dural vasodilation and sensitization of trigeminal neurons in anaesthetized rats", British Journal of Pharmacology, Jul. 2001, 16 pages.

Hayes et al., "Neuropathic Pain in the Perioperative Period", Neuropathic Pain 81, 1997, 15 pages.

English translation (Anonymous, "Palexia @ retard Retardtabletten", 2010, pp. 1-5, XP 002643645) 13 pages.

Boards of Appeal of the European Patent Office ; Decision of May 4, 2000, Case No. T 0233/96-3.3.2 (25 pages).

European Patent Office Boards of Appeal, Friction reduction additives and compositions thereof, Case No. G 2/88, Dec. 1989, 33 pages.

Written Opinion of the International Preliminary Examining Authority issued in PCT Application No. PCT/EP2012/001819 dated May 7, 2013, six pages.

Co-pending U.S. Appl. No. 15/243,271, filed Aug. 22, 2016.

European Search Report issued in counterpart European Application No. 11002810.7 dated Jul. 1, 2011 (11 pages).

Co-pending U.S. Appl. No. 13/438,410, filed Apr. 3, 2012.

English translation (Palexia Filmtabletten, Gruenethal, Aug. 19, 2010, 13 pages) previously filed on Oct. 3, 2016 (13 pages).

Baron, "CME: Diagnosis and Treatment of Neuropathic Pain", Dtsch Arztebl, 2006, pp. 1-16, vol. 103, No. 41.

Stahl, "Preemptive Analgesia: Is Pain Less Costly When You Pre-Pay for It?", Clinical Neuroscience Update, 2004, pp. 1591-1592, Physicians Postgraduate Press, Inc.

"Manual of Therapeutic Agents 2007", 2007, pp. 928-929 with English translation (9 pages).

European Search Report dated Jun. 21, 2011 (eleven (11) pages).

Gary J. Bennett et al., "A Peripheral Mononeuropathy in Rat that Produces Disorders of Pain Sensation Like Those Seen in Man", Elsevier, Pain, 33, (1988), pp. 87-107.

R. Lange et al., "Short Form-36 (SF-36) and Euroqol-5 Dimension (EQ-5D) Results from Randomized, Double-Blind Phase 3 Studies of Tapentadol Prolonged Release (PR) In Patients with Moderate to Severe Chronic Nociceptive and Neuropathic Pain", vol. 18, Oct. 1, 2010, pp. S147-S148, XP027316899.

T. M. Tzschentke et al., "Tapentadol hydrochloride. Analgesic, Mu-Opioid Receptor Agonist, Noradrenaline Reuptake Inhibitor", Drugs of the Future, 2006, vol. 31, No. 12, pp. 1053-1061, XP-002438122.

T. M. Tzschentke et al., "Tapentadol:Mitzwei Mechanismen in Einem Molekuel Wirksam Gegan Nozizeptive Und Neuropathische Schmerzen", vol. 25, No. 1, Feb. 1, 2011, pp. 19-25, XP009149538.

W. Schroeder et al., "Differential Contribution of Opioid and Noradrenergic Mechanisms of Tapentadol in Rat Models of

(56) References Cited

OTHER PUBLICATIONS

Nociceptive and Neuropathic Pain", European Journal of Pain, vol. 14, No. 8, Sep. 1, 2010, pp. 814-821, XP027224271.
T. Christoph et al., "Anti-Allodynic Activity of Tapentadol in a Rat Model of Neuropathic Pain Depends on Opioid and Noradrenergic, But Not Serotonergic, Mechanisms", European Journal of Pain, vol. 13, Sep. 1, 2009, p. S205.
Valerie Kayser et al., "Differential Anti-Neuropathic Pain Effects of Tetrodotoxin in Sciatic Nerve-Versus Infraorbital Nerve-Ligated Rats—Behavioral, Pharmacological and Immunohistochemical Ivestigations", Neuropharmacology, vol. 58, (2010) pp. 474-487.
Bart P. Vos et al., "Behavioral Evidence of Trigeminal Neuropathic Pain Following Chronic Constriction Injury to the Rat's Infraorbital Nerve", The Journal of Neuroscience, vol. 14, No. 5, May 1994, pp. 2708-2723.
Valerie Kayser et al., "The Antimigraine 5-HT 1B/1D Receptor Agonists, Sumatriptan, Zolmitriptan and Dihydroergotamine, Attenuate Pain-Related Behaviour in a Rat Model of Trigeminal Neuropathic Pain", British Journal of Pharmacology, vol. 137, (2002), pp. 1287-1297.
Xidao Wang et al., "TrkB Signaling is Required for Both the Induction and Maintenance of Tissue and Nerve Injury-Induced Persistent Pain", The Journal of Neuroscience, vol. 29, No. 17 Apr. 29, 2009, pp. 5508-5515.
Adalberto Merighi et al., "BDNF as a Pain Modulator", Progress in Neurobiology, vol. 85, (2008), Elsevier, pp. 297-317.
Lintner, C. PhD., "Stability of Pharmaceutical Products", Remington Chapter 82, pp. 1478-1486, 1985 (nine (9) sheets).
Erskine, C., Jr., "Quality Assurance and Control" Remington Chapter 83, pp. 1487-1491, 1985 (five (5) sheets).
Nairn, J.G. PhD., "Solutions, Emulsions, Suspensions and Extractives", Remington Chapter 84, pp. 1492-1517, 1985 (twenty-six (26) sheets).
Avis, K. DSc., "Parenteral Preparations", Remington Chapter 85, pp. 1518-1541, 1985 (twenty-four (24) sheets).
Turco et al., "Intravenous Admixtures", Remington Chapter 86, pp. 1542-1552, 1985 (eleven (11) sheets).
Mullins, J. PhD., "Ophthalmic Preparations", Remington Chapter 87, pp. 1553-1566, 1985 (fourteen (14) sheets).
Block, L. PhD., "Medicated Applications", Remington Chapter 88, pp. 1567-1584, 1985 (eighteen (18) sheets).
Rippie, E. PhD., "Powders", Remington Chapter 89, pp. 1585-1602, 1985 (eighteen (18) sheets).
King et al., "Oral Solid Dosage Forms", Remington Chapter 90, pp. 1603-1632, 1985 (thirty (30) sheets).
Porter, S. PhD., "Coating of Pharmaceutical Dosage Forms", Remington Chapter 91, pp. 1633-1643, 1985 (eleven (11) sheets).
Longer et al., "Sustained-Release Drug Delivery Systems", Remington Chapter 92, pp. 1644-1661, 1985 (eighteen (18) sheets).
Sclarra et al., "Aerosols", Remington Chapter 93, pp. 1662-1677, 1985 (sixteen (16) sheets).
Daniels et al., "A randomized, double-blind, placebo-controlled phase 3 study of the relative efficacy and tolerability of tapentadol IR and oxycodone IR for acute pain", Current Medical Research and Opinions, 2009, pp. 1551-1561, vol. 25, No. 6, Premier Research et al., Austin, TX.

Masuda, The Journal of Japanese Society for the Study of Chronic Pain, 2006, pp. 23-27, vol. 25, No. 1, Presented by Medical Online, Department of Anesthesiology, Showa University School of Medicine, with English abstract.
The Japanese Journal of Clinical and Experimental Medicine, 2001, pp. 91-94.
Jpn J Psychosom Med, 2010, pp. 1045-1050, vol. 50, No. 11, Presented by Medical Online, with English abstract.
Partial International Search Report (PCT/ISA/206) issued in PCT Application No. PCT/EP2012/001472 dated Jun. 6, 2012 (five pages).
International Search Report (PCT/ISA/220 & PCT/ISA/210) issued in PCT Application No. PCT/EP2012/001472 dated Aug. 3, 2012 (seven pages).
Written Opinion (PCT/ISA/237) issued in PCT Application No. PCT/EP2012/001472 dated Aug. 3, 2012 (13 pages).
Anonymous, "Palexia ® retard Retardtabletten", 2010, pages 1-5, XP-002643645.
Kehlet, "Do We Have the Tools to Prevent Phantom Limb Pain?", Anesthesiology, May 2011, pp. 1021-1024, vol. 114, No. 5.
International Search Report (PCT/ISA/220 & PCT/ISA/210) issued in PCT Application No. PCT/EP2012/001475 dated Jun. 27, 2012 (six pages).
Written Opinion (PCT/ISA/237) issued in PCT Application No. PCT/EP2012/001475 dated Jun. 27, 2012 (five pages).
Shou et al., "Oral Ralfinamide Suppresses Autonomy Following Hindpaw Deafferentation by Multiple Dorsal Rhizotomies, a Rat Model of CNS-Mediated Spontaneous Neuropathic Pain", Poster Sessions/European Journal of Pain, 2009, vol. 13, two pages, XP 26680911.
Bjelland et al., "The validity of the Hospital Anxiety and Depression Scale An updated literature review", Journal of Psychosomatic Research 52, 2002, pp. 69-77, Elsevier, English translation.
Nakamura, "Pain and Heart", Dental Diamond, 1999, two pages, vol. 24 (338), Partial translation.
Motoshima, "Experiences of Cases Associated with Pain", Clinical Psychiatry, 1996, two pages, vol. 25 (12), Partial translation.
Nadaoka, "Diagnosis of Pain Disorder based on Clinical Psychiatry", Pain and Clinical Treatment, 2001, two pages, vol. 1 (2), Partial translation.
Tanaka et al., New Pharmacology, published by Nankodo, 1997, two pages, Partial translation.
English translation of document C59 (Jpn J Psychosom Med, 2010, pp. 1045-1050, vol. 50, No. 11, Presented by Medical Online, with English abstract).
English translation of document C58 (The Japanese Journal of Clinical and Experimental Medicine, 2001, pp. 91-94.).
English translation of document C57 (Masuda, The Journal of Japanese Society for the Study of Chronic Pain, 2006, pp. 23-27, vol. 25, No. 1, Presented by Medical Online, Department of Anesthesiology, Showa University School of Medicine, with English abstract).
Arana et al., "Suicide-Related Events in Patients Treated with Antiepileptic Drugs", The new England Journal of Medicine, 2010, pp. 542-551.
Dworkin et al., "Multiple Pains and Psychiatric Disturbance, An Epidemiologic Investigation", Arch Gen Psychiatry, Mar. 1990, pp. 239-244, vol. 47.

* cited by examiner

USE OF TAPENTADOL FOR INHIBITING AND/OR TREATING DEPRESSION AND ANXIETY

CROSS REFERENCE TO RELATED APPLICATIONS

This application is a divisional of U.S. application Ser. No. 14/502,552, filed Sep. 30, 2014, which is a continuation of U.S. application Ser. No. 13/458,510, filed Apr. 27, 2012, which claims priority from U.S. provisional patent Application No. 61/480,621, filed Apr. 29, 2011, the entire disclosures of which are incorporated herein by reference. Priority is also claimed based on European patent application no. EP 11 003 508.6, filed Apr. 29, 2011, the entire disclosure of which is likewise incorporated herein by reference.

BACKGROUND OF THE INVENTION

The present invention relates to the use of tapentadol in the (i) treatment of pain, preferably of neuropathic pain, more preferably of neuropathic pain due to lumbar radiculopathy, in a subject suffering from depression and/or from anxiety, and/or in the (ii) treatment or the inhibition of depression and/or of anxiety.

Tapentadol (CG5503), the chemical name for which is (−)-(1R,2R)-3-(3-dimethylamino-1-ethyl-2-methyl-propyl)-phenol, is a synthetic, centrally-acting analgesic that is effective for the treatment of moderate to moderately-severe acute or chronic pain. The compound can be employed as the free base or its physiologically acceptable salts and solvates. Preparation of the free base is known e.g. from U.S. Pat. No. 6,248,737 (=EP 693,475).

Tapentadol is a centrally acting analgesic with a dual mode of action consisting of μ-opioid receptor (MOR) agonism and norepinephrine (NE) reuptake inhibition. The efficacy, safety, and pharmacokinetic profile of tapentadol indicate that the drug is useful in treating acute as well as chronic pain.

Subjects suffering from pain often fall into depression and anxiety, especially if the pain is chronic or neuropathic. In patients with chronic or neuropathic pain 8 to 50% have been reported to have current major depression (Smith G R, The epidemiology and treatment of depression when it co-exists with somatoform disorders, somatization or pain. Gen Hosp Psychiatry 1992, 14: 265-276). In another analysis of 1,016 patients, the prevalence of depression was 12% in individuals with 3 or more pain complaints (Dworkin S F et al., Multiple pains and psychiatric disturbance: an epidemiological investigation. Arch Gen Psychiatry 1990, 47: 239-244).

The most serious consequences of major depression are suicide and increased rates of suicidal ideation and suicide completion have been reported by patients suffering from chronic pain conditions (Magni et al., Suicidality in chronic abdominal pain; an analysis of the Hispanic Health and Nutrition Examination Survey (HHANES). Pain 1998, 76: 137-144). Oncology patients with concomitant pain and depression were significantly more likely to request assistance in committing suicide as well as actively taking steps to commit suicide. In contrast those with pain in the absence of depression were unlikely to request the intervention of euthanasia and physician-assisted suicide (Emmanuel et al., Euthanasia and physician assisted suicide; attitudes and experiences of oncology patients, oncologists and the public. Lancet 1996, 347: 1810).

On the other hand, subjects suffering from depression and/or anxiety often have pain symptoms, which can be attributed to a somatoform disorder (psychogenic pain). The pain symptoms are physical symptoms, which typically do not have an identifiable physical origin. Instead, they are the result of internal psychological conflicts that are unconsciously expressed as physical signs.

It is evident that subjects suffering from depression and/or anxiety induced by pain or inducing pain symptoms are in need of medicaments for the treatment of both, the depression and/or anxiety as well as the pain.

US 2009/0215809 discloses pharmaceutical compositions comprising a crystalline prodrug of an antiepileptic drug, namely pregabalin ((S)-3-(Aminomethyl)-5-methylhexanoic acid) for the treatment of certain diseases and disorders, including, for example, neuropathic pain, generalized anxiety disorder, fibromyalgia, migraine, hot flashes, restless legs syndrome, and sleep disorders. The pharmaceutical composition may additionally comprise an opioid agonist selected from tramadol, tapentadol, and oxycodone as a second therapeutic agent.

Similarly, U.S. Pat. No. 7,868,043 discloses pharmaceutical compositions comprising a mesophasic pregabalin prodrug and methods of use thereof.

US 2010/0297181 discloses methods for treating epilepsy, mental disorders and/or deficits in sensory organ by administering to patients therapeutically effective amounts of AMPA receptor antagonists, i.e. antiepileptic drugs, in combination with one or more other active ingredients useful for treating epilepsy, mental disorders and/or deficits in the sensory organ. Tapentadol is mentioned in a list of suitable active ingredients to be administered in combination with AMPA receptor antagonists. As mental disorders, mood disorders, such as depressions, are listed.

The use of antiepileptic drugs, however, can be detrimental because it has been found that it can be associated with a significantly increased risk for suicide-related events in patients with depression (Arana et al., Suicide-related events in patients treated with antiepileptic drugs. N Engl J Med 2010, 363: 542-551). Furthermore, a pharmaceutical composition comprising a combination of an antiepileptic and tapentadol can be disadvantageous because of adverse events caused by each drug itself and due to interactions of the drugs with each other, respectively.

Accordingly, there is a need for pharmaceutical compositions comprising a single pharmacologically active ingredient for use in the treatment of pain in a subject suffering from depression and/or anxiety, and/or for use in the treatment or the inhibition of depression and/or anxiety, wherein the single pharmacologically active ingredient may simultaneously or sequentially act as an antidepressant and as an analgesic.

US 2009/0306050 discloses compounds, such as lofepramine, exhibiting an activity as a potent norepinephrine (NE) reuptake inhibitor, and an activity at the dopamine D2 receptor sites. It was found that these special compounds are effective in the treatment and inhibition of various diseases and disorders associated with norepinephrine reuptake, such as pain predominant-type depression and depression secondary to chronic or neuropathic pain. However, antidepressants such as lofepramine exhibit several nuisance side effects and several warnings have been reported.

M. Afilalo et al., Clin. Drug Investig. 2010, 30(8), 489-505 discloses information concerning the efficacy and safety of tapentadol extended release compared with oxycodone controlled release for the management of moderate to severe chronic pain related to osteoarthritis of the knee.

B. Kupferwasser et al., Osteoarthritis and Cartilage 2009, Vol. 17, Supplement 1, 179 discloses an evaluation of long-term treatment with tapentadol extended release and oxycodone controlled release in patients with chronic low back or osteoarthritis pain.

R. Lange et al., Osteoarthritis and Cartilage 2010, Vol. 18, Supplement 2, 147-148 discloses results from randomized, double-blind phase 3 studies of tapentadol prolonged release in patients with moderate to severe chronic nociceptive and neuropathic pain.

B. Kupferwasser et al., Osteoarthritis and Cartilage 2010, Vol. 18, Supplement 2, 149 discloses information concerning the health status of patients who received tapentadol prolonged release during an open-label extension study.

S. Schwartz et al., Current Medical Research & Opinion, 27(1), 2011, 151-162 discloses results of a randomized-withdrawal, placebo-controlled trial concerning safety and efficacy of tapentadol ER in patients with painful diabetic peripheral neuropathy.

Accordingly, there remains a need for improved pharmaceutical compositions comprising a single pharmacologically active ingredient useful for treating pain and simultaneously or sequentially treating depression and/or anxiety.

SUMMARY OF THE INVENTION

It is an object of the invention to provide medicaments for the treatment and inhibition of depression and/or of anxiety that have advantages compared to the medicaments of the prior art. This object has been achieved by the invention as described and claimed hereinafter.

While the analgesic efficacy of tapentadol is generally known, it has surprisingly been found that tapentadol is also effective in the treatment or inhibition of depression and/or of anxiety, preferably of depression and/or of anxiety that is induced by pain in a subject suffering from pain, and of depression and/or of anxiety inducing psychogenic pain.

In particular, in clinical trials concerning the efficacy of tapentadol against low back pain, depression (measured with HADS) was observed as undesired side effect. While in general, the occurrence of this symptom was at the borderline with respect to its clinical relevance, in the patient sub-population suffering from neuropathic pain, i.e. suffering from low back pain with a neuropathic component, a significant occurrence of depression was observed and tapentadol unexpectedly provided significant improvement.

In a first aspect, the invention is directed to the use of tapentadol in
(i) the treatment of pain, preferably of neuropathic pain, more preferably of neuropathic pain due to lumbar radiculopathy, in a subject suffering from depression and/or from anxiety, and/or
(ii) the treatment or inhibition of depression and/or of anxiety,
with the proviso tapentadol is not administered in combination with an antiepileptic.

Thus, the invention relates to, inter alia, the use of tapentadol in
a) the treatment of pain, preferably of neuropathic pain, more preferably of neuropathic pain due to lumbar radiculopathy, in a subject suffering from depression and/or from anxiety;
b) the treatment of depression and/or of anxiety in a subject suffering from depression and/or from anxiety;
c) the treatment of depression and/or of anxiety in a subject suffering from pain, preferably from neuropathic pain, more preferably from neuropathic pain due to lumbar radiculopathy;
d) the inhibition of depression and/or of anxiety;
e) the treatment of pain, preferably of neuropathic pain, more preferably of neuropathic pain due to lumbar radiculopathy, and the simultaneous treatment of depression and/or of anxiety; and/or
f) the treatment of pain, preferably of neuropathic pain, more preferably of neuropathic pain due to lumbar radiculopathy, and simultaneous inhibition of depression and/or of anxiety.

A second aspect of the invention relates to a method for
(i) the treatment of pain, preferably of neuropathic pain, more preferably of neuropathic pain due to lumbar radiculopathy, in a subject suffering from depression and/or from anxiety, and/or
(ii) the treatment or the inhibition of depression and/or of anxiety,
comprising the administration of an effective amount of tapentadol,
with the proviso tapentadol is not administered in combination with an antiepileptic.

For the purpose of the specification, "tapentadol" is intended to include (−)-(1R,2R)-3-(3-dimethylamino-1-ethyl-2-methyl-propyl)-phenol, its physiologically acceptable salts and solvates thereof. Suitable physiologically acceptable salts include salts of inorganic acids, such as hydrochloric acid (tapentadol HCl), hydrobromic acid and sulfuric acid, and salts of organic acids, such as methane sulfonic acid, fumaric acid, maleic acid, acetic acid, oxalic acid, succinic acid, malic acid, tartaric acid, mandelic acid, lactic acid, citric acid, glutamic acid, acetylsalicylic acid, nicotinic acid, aminobenoic acid, Hp ponic acid, hippuric acid and asparaginic acid. The preferred salt is the hydrochloride salt.

For the purpose of the specification, unless expressly stated otherwise, doses of tapentadol relate to the free base. Thus, when a physiologically acceptable salt of tapentadol is used instead, its dose has to be adapted to the equivalent dose of the free base. For example, a dose of "200 mg" means an amount of 200 mg of the free base or any equivalent amount of a physiologically acceptable salt or solvate corresponding to 200 mg of the free base (e.g. about 233 mg of the hydrochloride). If not expressly stated otherwise, doses are "per administration", not "per day".

The term "depression" is known to persons skilled in the art. Depression is a common mental disorder that presents with depressed mood, loss of interest or pleasure, feelings of guilt or low self-worth, disturbed sleep or appetite, low energy, and poor concentration. These problems can become chronic or recurrent and lead to substantial impairments in an individual's ability to take care of his or her everyday responsibilities. At its worst, depression can lead to suicide. Depression occurs in persons of all genders, ages, and backgrounds. In this regard it can further be referred e.g. to the International Classification of Diseases (ICD-10), particularly to its Chapter V. As used in the specification, the term "depression" preferably covers hereditary depressions and depressions, which represent a reaction of stressors in the environment, or both. Preferably, pain is regarded as stressor in the environment. Furthermore, the term "depression" also covers depressive disorders, such as mood disorder, major depressive disorder, and dysthymic disorder. Preferably, the term "depression" also relates to depression induced by pain, i.e. depression that arises from pain in a subject suffering from pain. The depression is typically caused by the chronic nature of the pain.

As used herein, the "depression score" is a value determining the degree of the depression. The scale of depression scores covers the range from 0 to 21, wherein the degree of the depression is high in case of high values and low in case of low values. In a group of tested subjects, typically the mean or mediate values of depression scores are determined. The mean value is the sum of all depression scores divided by the number of subjects. The mediate value is the middle depression score in the set of determined scores. Preferably, the "depression score" is defined as in the experimental section.

The term "anxiety" is known to the skilled person. Anxiety is one of the feelings one experiences when under stress; physical, social, economic, psychological. Anxiety results in a feeling of impending doom, fear (which can be intense), dryness of mouth, sweating, restlessness, racing heart, butterflies in the stomach, itching and tingling all over the body, shortness of breath, having to visit the bathroom repeatedly, inability to concentrate, make decisions, carry out work, eat or sleep. In this regard it can further be referred e.g. to the International Classification of Diseases (ICD-10), particularly to its Chapter V. As used herein, the term "anxiety" relates to an anxiety disorder. Preferably, the term "anxiety" also covers panic disorder, generalized anxiety disorder, and somatoform disorders. Preferably, the term "anxiety" also relates to anxiety induced by pain, i.e. anxiety that arises from pain in a subject suffering from pain. The anxiety is typically caused by the chronic nature of the pain.

As used herein, the "anxiety score" is a value determining the degree of the depression. The scale of anxiety scores covers the range from 0 to 21, wherein the degree of the anxiety is high in case of high values and low in case of low values. In a group of tested subjects, typically the mean or mediate values of anxiety scores are determined and referred to. The mean value is the sum of all anxiety scores divided by the number of subjects. The mediate value is the middle anxiety score in the set of determined scores. Preferably, the "anxiety score" is defined as in the experimental section.

As used herein the terms "inhibit" and "inhibition" refer only to a retarding or lessening of a condition.

As used herein the term "antiepileptic" relates to drugs used in the treatment of epilepsy. The term "antiepileptic" preferably also covers "anticonvulsants", which are used in the treatment of epileptic seizures. Thus, the terms "antiepileptic", "anticonvulsant" and "anti-seizure drug" are to be understood as synonyms. According to the ATC-index of the "WHO Collaborating Center for Drug Statistics Methodology" antiepileptics (N03A) cover barbiturates and derivatives, hydantoin derivatives, oxazolidine derivatives, succinimide derivatives, benzodiazepine derivatives, carboxamide derivatives, fatty acid derivatives and other antiepileptics such as pregabalin (N03AX16). According to US 2010/0297181 AMPA receptor antagonists such as 1,2-dihydropyridine compounds also exhibit an anti-seizure effect and are useful in the treatment of epilepsy. Thus, AMPA receptor antagonists also fall under the term "antiepileptic". Dihydropyridine derivatives are also known as selective calcium channel blockers with mainly vascular effects (C08CA) according to the ATC-index of the "WHO Collaborating Center for Drug Statistics Methodology". Thus, calcium channel blockers are also considered as being covered by the term "antiepileptic" in the specification.

As used herein, the term "psychogenic pain" preferably refers to painful symptoms, which are the result of internal psychological conflicts. These unconsciously expressed physical symptoms typically do not have an identifiable origin. Instead, the painful symptoms are the result of a somatoform disorder, also known as pain disorder. The "somatization" of pain belongs to painful symptoms of depressions and can be defined as the disease "pain predominant-type depression", wherein the depression manifests itself predominantly in the "somatization" of pain. Preferably, the pain disorder, i.e. the "somatization of pain", also includes hypersensitivity to pain. Furthermore, the pain disorder can be accompanied by hypochondriasis.

As used herein, the "pain score" is a value determining the degree of pain or a mixture of pains in a subject is suffering from pain. The scale of pain scores covers the range from 0 to 21, wherein the degree of pain is high in case of high values and low in case of low values. In a group of tested subjects, typically the mean or mediate values of pain scores are determined and referred to. The mean value is the sum of all pain scores divided by the number of subjects. The mediate value is the middle pain score in the set of determined scores. Accordingly, the "neuropathic pain score" is a value determining the degree of neuropathic pain, and the "nociceptive pain score" is a value determining the degree of nociceptive pain. Preferably, the "pain score" is defined as in the experimental section.

According to the invention, tapentadol is used in the
(i) treatment of pain in a subject suffering from depression and/or from anxiety, and/or
(ii) treatment or the inhibition of depression and/or of anxiety,
with the proviso tapentadol is not administered in combination with an antiepileptic.

Preferably, tapentadol is used in the
(i) treatment of neuropathic pain, more preferably of neuropathic pain due to lumbar radiculopathy, in a subject suffering from depression and/or from anxiety, and/or
(ii) treatment or the inhibition of depression and/or of anxiety in a subject suffering from neuropathic pain, more preferably from neuropathic pain due to lumbar radiculopathy,
preferably with the proviso that tapentadol is not administered in combination with an antiepileptic.

In one preferred embodiment, tapentadol is used in the treatment of pain in a subject suffering from depression and/or from anxiety, wherein the pain is neuropathic pain, preferably polyneuropathic pain, more preferably diabetic polyneuropathic pain.

In another preferred embodiment, tapentadol is used in the treatment of pain in a subject suffering from depression and/or from anxiety, wherein the pain is low back pain, preferably pain due to lumbar radiculopathy, having a neuropathic component, particularly a mononeuropathic component or a polyneuropathic component. The neuropathic component can be assessed e.g. by painDETECT positive (for further details, it is referred to the experimental section).

In a preferred embodiment, tapentadol is used in the treatment of pain in a subject that can be considered opioid naïve. In a preferred embodiment, tapentadol is used in the treatment of pain in a subject that has been pre-treated with opioids, preferably weak opioids.

In a preferred embodiment, tapentadol is used in the treatment of pain in a subject suffering from depression and/or from anxiety, wherein the pain is causative for depression and/or for anxiety, i.e. the pain induces depression and/or anxiety. Preferably, the pain and depression and/or anxiety are simultaneously or sequentially treated. More preferably, the pain, which is causative for depression and/or for anxiety is a mixture of nociceptive and neuropathic pain, and is simultaneously or sequentially treated with depression and/or anxiety. Most preferably, the pain, which is causative for depression and/or anxiety is neuropathic pain, and is simultaneously or sequentially treated with depression and/or anxiety.

In another preferred embodiment, tapentadol is used in the treatment of depression and/or of anxiety in a subject suffering from depression and/or from anxiety, which cannot be attributed to a pain. Preferably, the depression and/or anxiety can be attributed to a disability, to a chronic disease, to chemotherapy, to a hospital stay, to side effects of a medicament, and/or the like.

In another preferred embodiment, tapentadol is used in the treatment of depression and/or of anxiety in a subject suffering from pain, wherein depression and/or anxiety is causative for the pain, i.e. depression and/or anxiety occurs with pain symptoms. The pain symptoms may be regarded as psychogenic pain. Preferably, the psychogenic pain and depression and/or anxiety are simultaneously or sequentially treated.

In another preferred embodiment, tapentadol is used in the inhibition of depression and/or of anxiety. Preferably, depression and/or anxiety are expected to develop due to a disability, to a chronic disease, to chemotherapy, to a hospital stay, to side effects of a medicament, and/or the like.

In another preferred embodiment, tapentadol is used in the treatment of pain and the simultaneous treatment of depression and/or of anxiety. Preferably, the pain is chronic pain. More preferably, the pain is selected from the group consisting of neuropathic pain, nociceptive pain, psychogenic pain, phantom pain, and mixtures thereof. Still more preferably, the pain is a mixture of nociceptive and neuropathic pain. Most preferably, the pain is neuropathic pain.

In another preferred embodiment, tapentadol is used in the treatment of pain and the simultaneous inhibition of depression and/or anxiety. Preferably, the pain is chronic pain. More preferably, the pain is selected from the group consisting of neuropathic pain, nociceptive pain, psychogenic pain, phantom pain, and mixtures thereof. Still more preferably, the pain is a mixture of nociceptive and neuropathic pain. Most preferably, the pain is neuropathic pain.

According to the invention, tapentadol is not administered in combination with an antiepileptic. This is advantageous because the use of antiepileptic drugs for the treatment of a subject suffering from depression and/or anxiety is undesired. It has been found that antiepileptic drugs can be associated with a significantly increased risk for suicide-related events in patients with depression. Preferably, tapentadol is not administered in combination with anticonvulsants and anti-seizure drugs. More preferably, tapentadol is not administered in combination with an antiepileptic selected from the group consisting of barbiturates and derivatives, hydantoin derivatives, oxazolidine derivatives, succinimide derivatives, benzodiazepine derivatives, carboxamide derivatives, fatty acid derivatives and other antiepileptics such as pregabalin. Most preferably, tapentadol is not administered in combination with pregabalin.

In another preferred embodiment, tapentadol is not administered in combination with AMPA receptor antagonists. AMPA receptor antagonists such as 1,2-dihydropyridines are classified as antiepileptics according to US 2010/0297181, which is incorporated by reference. Preferably, tapentadol is not administered in combination with any of the antiepileptic AMPA receptor antagonists mentioned in US 2010/0297181. More preferably, tapentadol is not administered in combination with 1,2-dihydropyridines or derivatives thereof. Dihydropyridines are also known as selective calcium channel blockers with mainly vascular effects (C08CA) according to the ATC-index of the "WHO Collaborating Center for Drug Statistics Methodology". Consequently, tapentadol is preferably also not administered in combination with selective calcium channel blockers with mainly vascular effects. Most preferably, tapentadol is administered neither with an antiepileptic nor a calcium channel blockers.

In one preferred embodiment, tapentadol is administered as the only pharmacologically active ingredient in a medicament (medication). Preferably, tapentadol is administered via a route selected from the group consisting of orally, buccally, sublingually, transmucosally, intralumbally, intraperitoneally, transdermally, intraveneously, intramusculously, intragluteally, intracutaneously and subcutaneously. More preferably, tapentadol is administered orally.

In another preferred embodiment, tapentadol is administered once or twice daily and/or at a daily dose within the range of from 25 to 600 mg.

In another preferred embodiment, the dose of tapentadol to be administered once daily or twice daily in the course of each administration amounts to 50 mg (±75%), more preferably 50 mg (±50%), still more preferably 50 mg (±30%), yet more preferably 50 mg (±20%), most preferably 50 mg (±10%), and in particular 50 mg (±5%).

In another preferred embodiment, the dose of tapentadol to be administered once daily or twice daily in the course of each administration amounts to 100 mg (±75%), more preferably 100 mg (±50%), still more preferably 100 mg (±30%), yet more preferably 100 mg (±20%), most preferably 100 mg (±10%), and in particular 100 mg (±5%).

In still another preferred embodiment, the dose of tapentadol to be administered once daily or twice daily in the course of each administration amounts to 150 mg (±75%), more preferably 150 mg (±50%), still more preferably 150 mg (±30%), yet more preferably 150 mg (±20%), most preferably 150 mg (±10%), and in particular 150 mg (±5%).

In yet another preferred embodiment, the dose of tapentadol to be administered once daily or twice daily in the course of each administration amounts to 200 mg (±75%), more preferably 200 mg (±50%), still more preferably 200 mg (±30%), yet more preferably 200 mg (±20%), most preferably 200 mg (±10%), and in particular 200 mg (±5%).

In a preferred embodiment, the dose of tapentadol to be administered once daily or twice daily in the course of each administration amounts to 250 mg (±75%), more preferably 250 mg (±50%), still more preferably 250 mg (±30%), yet more preferably 250 mg (±20%), most preferably 250 mg (±10%), and in particular 250 mg (±5%).

In another preferred embodiment, tapentadol is used in the treatment of pain in a subject suffering from depression, wherein the pain is selected from the group consisting of pain being or being associated with panic disorder [episodic paroxysmal anxiety] [F41.0]; dissociative [conversion] disorders [F44]; persistent somatoform pain disorder [F45.4]; pain disorders exclusively related to psychological factors [F45.41]; nonorganic dyspareunia [F52.6]; other enduring personality changes [F62.8]; sadomasochism [F65.5]; elaboration of physical symptoms for psychological reasons [F68.0]; migraine [G43]; other headache syndromes [G44]; trigeminal neuralgia [G50.0]; atypical facial pain [G50.1]; phantom limb syndrome with pain [G54.6]; phantom limb syndrome without pain [G54.7]; acute and chronic pain, not elsewhere classified [G89]; ocular pain [H57.1]; otalgia [H92.0]; angina pectoris, unspecified [I20.9]; other specified disorders of nose and nasal sinuses [J34.8]; other diseases of pharynx [J39.2]; temporomandibular joint disorders

[K07.6]; other specified disorders of teeth and supporting structures [K08.8]; other specified diseases of jaws [K10.8]; other and unspecified lesions of oral mucosa [K13.7]; glossodynia [K14.6]; other specified diseases of anus and rectum [K62.8]; pain in joint [M25.5]; shoulder pain [M25.51]; sacrococcygeal disorders, not elsewhere classified [M53.3]; spine pain [M54.]; radiculopathy [M54.1]; cervicalgia [M54.2]; sciatica [M54.3]; low back pain [M54.5]; pain in thoracic spine [M54.6]; other dorsalgia [M54.8]; dorsalgia, unspecified [M54.9]; other shoulder lesions [M75.8]; other soft tissue disorders, not elsewhere classified [M79]; myalgia [M79.1]; neuralgia and neuritis, unspecified [M79.2]; pain in limb [M79.6]; other specified disorders of bone [M89.8]; unspecified renal colic [N23]; other specified disorders of penis [N48.8]; other specified disorders of male genital organs [N50.8]; mastodynia [N64.4]; pain and other conditions associated with female genital organs and menstrual cycle [N94]; mittelschmerz [N94.0]; other specified conditions associated with female genital organs and menstrual cycle [N94.8]; pain in throat and chest [R07]; pain in throat [R07.0]; chest pain on breathing [R07.1]; precordial pain [R07.2]; other chest pain [R07.3]; chest pain, unspecified [R07.4]; abdominal and pelvic pain [R10]; acute abdomen [R10.0]; pain localized to upper abdomen [R10.1]; pelvic and perineal pain [R10.2]; pain localized to other parts of lower abdomen [R10.3]; other and unspecified abdominal pain [R10.4]; flatulence and related conditions [R14]; abdominal rigidity [R19.3]; other and unspecified disturbances of skin sensation [R20.8]; pain associated with micturition [R30]; other and unspecified symptoms and signs involving the urinary system [R39.8]; headache [R51]; pain, not elsewhere classified [R52]; acute pain [R52.0]; chronic intractable pain [R52.1]; other chronic pain [R52.2]; pain, unspecified [R52.9]; other complications of cardiac and vascular prosthetic devices, implants and grafts [T82.8]; other complications of genitourinary prosthetic devices, implants and grafts [T83.8]; other complications of internal orthopaedic prosthetic devices, implants and grafts [T84.8]; other complications of internal prosthetic devices, implants and grafts, not elsewhere classified [T85.8]; wherein the information in brackets refers to the classification according to ICD-10.

In a preferred embodiment, the invention relates to the inhibition or treatment of pain selected from the aforementioned list of forms of pain according to ICD-10, irrespective of whether the subject simultaneously suffers from depression and/or anxiety or not.

In a particularly preferred embodiment, the invention relates to the inhibition or treatment of pain, preferably neuropathic pain, more preferably neuropathic pain due to lumbar radiculopathy, either in a subject simultaneously suffering from depression and/or anxiety; or in a subject simultaneously suffering neither from depression nor from anxiety.

Lumbar radiculopathy is a nerve irritation caused by damage to the discs between the vertebrae. Damage to the disc occurs because of degeneration of the outer ring of the disc, traumatic injury, or both. As a result, the central softer portion of the disc can rupture (herniate) through the outer ring of the disc and abut the spinal cord or its nerves as they exit the bony spinal column. This rupture is what causes the commonly recognized pain of "sciatica" that shoots down the leg.

Preferably, the tapentadol is used to treat moderate or severe pain. More preferably, the tapentadol is used to treat severe pain.

In another preferred embodiment, the pain is paroxysmal or constant. Preferably, the tapentadol is used to treat pain which is constantly present.

In another preferred embodiment, the pain is central or peripheral. Preferably, the pain is central.

In another preferred embodiment, the pain is chronic pain. Preferably, the subject has experienced the pain for at least a week, preferably at least a month, more preferably at least three months, still more preferably at least six months, and most preferably at least a year. More preferably, the pain has increased during the time the subject has experienced the pain. Most preferably, the pain has had an intermittent course during this time.

In a preferred embodiment, the chronic pain is selected from the group consisting of cancer pain, chemotherapy-induced pain, upper back pain, back pain, inflammatory pain including pain associated with rheumatic diseases, arthritic pain, ankylosing spondylitis pain, myofascial pain, pain associated with musculo-skeletal disorders, muscle pain, skeletal pain, joint pain, chronic pain associated with fibromyalgia, pain from strains/sprains, persistent post-operative pain, persistent posttraumatic pain, renal colic pain, irritable bowel syndrome-related pain, gastrointestinal pain, pelvic pain, abdominal pain, ischemic pain, angina pain, pain associated with claudication, pain accompanying myocardial infarction, vascular pain, pain associated with central nervous system trauma, facial pain, migraine-related pain, headache-related pain, orofacial pain, persistent pain deriving from damaged or inflamed somatic tissue, and combinations thereof. Preferably, the chronic pain is back pain, more preferably low back pain. Preferably, the chronic low back pain is nociceptive pain, neuropathic pain, or a mixture thereof, more preferably, the chronic low back pain is nociceptive mixed with neuropathic low back pain.

In another preferred embodiment, the pain is selected from neuropathic pain, nociceptive pain, psychogenic pain, phantom pain and mixtures thereof. Nociceptive pain may be causative for depression and/or for anxiety, i.e. induce depression and/or anxiety, whereas neuropathic pain, and phantom pain may be either causative for or resulting from depression and/or anxiety. Psychogenic pain typically results from depression and/or from anxiety, i.e. psychogenic pain may be regarded as a symptom of depression and/or anxiety.

Nociceptive pain is caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). Nociceptive pain may also be divided into "visceral," "deep somatic" and "superficial somatic" pain. Visceral pain originates in the viscera (organs) and often is extremely difficult to locate, and nociception from some visceral regions produces "referred" pain, where the sensation is located in an area distant from the site of the stimulus. Deep somatic pain is initiated by stimulation of nociceptors in ligaments, tendons, bones, blood vessels, fasciae and muscles, and is dull, aching, poorly-localized pain. Examples include sprains and broken bones. Superficial pain is initiated by activation of nociceptors in the skin or superficial tissues, and is sharp, well-defined and clearly located. Examples of injuries that produce superficial somatic pain include minor wounds and minor (first degree) burns.

Neuropathic pain is believed to be caused by a primary lesion or dysfunction in the nervous system. Neuropathic pains have been categorized as peripheral neuropathic pain, due to lesion of the peripheral nervous system and central pain following lesions of the central nervous system. The prevalence of neuropathic pain is estimated to be about 1%. Neuropathic pain has been shown to be rather therapy resistant. Accordingly, neuropathic pain has a high potential of inducing depressions in a subject experiencing neuropathic pain.

In another preferred embodiment, the pain is neuropathic pain, nociceptive pain or a mixture thereof. More preferably, the pain is neuropathic pain.

In a preferred embodiment, the neuropathic pain is selected from the group consisting of diabetic neuralgia, monoradiculopathies, trigeminal neuralgia, post-herpetic neuralgia, persistent postoperative or posttraumatic pain, hyperalgia, allodynia, fibromyalgia, complex regional pain syndrome (CRPS), pain associated with multiple sclerosis, AIDS-related neuropathy, thalamic pain, paraplegic pain caused by myelopathy, anesthesia dolorosa, low back pain, reflex sympathetic dystrophy/causalgia (nerve trauma), cancer pain, chemotherapy-induced pain, post-thoracotomy pain, entrapment neuropathy (e.g., carpal tunnel syndrome), and peripheral neuropathy (widespread nerve damage).

In one preferred embodiment, the neuropathic pain is polyneuropathic pain. Preferably, the pain is diabetic polyneuropathic pain.

In another preferred embodiment, the pain is a mixture of neuropathic and nociceptive pain, wherein the neuropathic pain score is higher than the nociceptive pain score. Preferred values for the neuropathic pain scores and nociceptive pain scores are summarized as preferred embodiments E1 to E6 below.

|  | E1 | E2 | E3 | E4 | E5 | E6 |
|---|---|---|---|---|---|---|
| Neuropathic pain score | ≥1 | ≥3 to 21 | 3 to 21 | 5 to 20 | 5 to 15 | 5 to 15 |
| Nociceptive pain score | ≥0 | 1 to 20 | 1 to 10 | 1 to 10 | 1 to 5 | 0 |

In another preferred embodiment, the pain is mainly neuropathic pain, wherein neuropathic pain score is preferably in the range of from 1 to 21, still more preferably from 3 to 21, yet more preferably from 5 to 20, most preferably from 5 to 15.

In another preferred embodiment, the depression and/or anxiety is induced by pain in a subject suffering from pain, wherein the pain is preferably as defined above.

In another preferred embodiment, the depression and/or anxiety induces psychogenic pain. Preferably, the psychogenic pain is back pain, chest pain, headache, muscle pain or a non-specific pain or ache, and can be regarded as a symptom for depression and/or anxiety.

In another preferred embodiment, the depression and/or anxiety induces one or more symptoms selected from the group consisting of depressed affect, anxiety, insomnia, suicidal thoughts, social inhibition, loss of energy, hopelessness, anhedonia, mood disturbances, irritability, disability, gastrointestinal disturbances, skin reactions, back pain, chest pain, headache, muscle pain and non-specific pains and aches.

The depression and/or anxiety a subject suffers from can be determined by the depression and/or the anxiety scores respectively. The initial depression and anxiety scores can be compared to the respective scores after the administration of certain amounts of tapentadol. Furthermore, the depression and anxiety scores can be assigned to certain pains. The mean and the mediate values for the depression and anxiety scores can be determined for a number of subjects. A reduction of these values indicates a decrease of depression and/or anxiety respectively.

In a preferred embodiment, the depression score is higher than the anxiety score. The values for the depression scores and anxiety scores are summarized as preferred embodiments E7 to E12 below.

|  | E7 | E8 | E9 | E10 | E11 | E12 |
|---|---|---|---|---|---|---|
| Depression score | ≥1 | 3 to 21 | 3 to 15 | 5 to 10 | 5 to 12 | 5 to 10 |
| Anxiety score | ≥0 | 1 to 20 | 1 to 10 | 1 to 8 | 3 to 8 | 3 to 5 |

In a preferred embodiment, tapentadol is used in the treatment of pain in a subject suffering from depression and/or from anxiety, wherein the depression and/or anxiety is simultaneously or sequentially treated, resulting in a reduction of the depression and anxiety scores and the pain scores. The values for the depression scores and anxiety scores as well as the pain scores, i.e. neuropathic and nociceptive pain scores in a subject are summarized as preferred embodiments E13 to E20 below.

|  | E13 | E14 | E15 | E16 | E17 | E18 | E19 | E20 |
|---|---|---|---|---|---|---|---|---|
| Depression score | ≥1 | 3 to 21 | 3 to 15 | 5 to 10 | 5 to 12 | 5 to 10 | 5 to 10 | 5 to 10 |
| Anxiety score | ≥0 | 1 to 20 | 1 to 10 | 1 to 10 | 3 to 8 | 3 to 8 | 3 to 8 | 3 to 5 |
| Neuropathic pain score | ≥1 | 3 to 21 | 3 to 21 | 5 to 20 | 5 to 15 | 5 to 15 | 5 to 10 | 5 to 10 |
| Nociceptive pain score | ≥0 | 1 to 20 | 1 to 15 | 1 to 10 | 1 to 5 | 0 | 0 | 0 |

Preferably, the reduction of anxiety is dependent on the pain the anxiety is associated with. The values for the anxiety scores before (initial) and after (final) the administration of tapentadol to a subject suffering from anxiety are summarized as preferred embodiments E21 to E25 below.

|  | E21 | E22 | E23 | E24 | E25 |
|---|---|---|---|---|---|
| Anxiety score associated with nociceptive pain | initial: 2 to 20 final: <90% of initial value | initial: 2 to 20 final: <80% of initial value | initial: 2 to 9 final: 1 to 8 | initial: 4 to 7 final: 3 to 6 | initial: 5.9 (±1) final: 4.5 (±1) |
| Anxiety score associated with neuropathic | initial: 2 to 20 final: <80% | initial: 2 to 20 final: <65% | initial: 4 to 11 final: | initial: 6 to 9 final: | initial: 7.9 (±1) final: |

|  | E21 | E22 | E23 | E24 | E25 |
|---|---|---|---|---|---|
| (presumed pain component) | of initial value | of initial value | 1 to 8 | 3 to 6 | 4.8 (±1) |
| Anxiety score associated with neuropathic (defined) | initial: 2 to 20 final: <80% of initial value | initial: 2 to 20 final: <70% of initial value | initial: 5 to 12 final: 1 to 8 | initial: 7 to 10 final: 3 to 6 | initial: 8.3 (±1) final: 4.5 (±1) |

Preferably, the time period between the determination of the initial and the final anxiety score is 6 months, more preferably 3 months, still more preferably 30 days, yet more preferably 20 days, most preferably 10 days. Furthermore, the daily dosage of tapentadol is preferably within the range of from 25 to 600 mg, preferably from 50 to 300 mg, more preferably from 50 to 150 mg.

Preferably, the reduction of depression is dependent on the pain the depression is associated with. The values for the depression scores before (initial) and after (final) the administration of tapentadol to a subject suffering from depression are summarized as preferred embodiments E21 to E25 below.

|  | E26 | E27 | E28 | E29 | E30 |
|---|---|---|---|---|---|
| Depression score associated with nociceptive | initial: 2 to 20 final: <95% of initial value | initial: 2 to 20 final: <85% of initial value | initial: 3 to 10 final: 1 to 8 | initial: 5 to 8 final: 3 to 6 | initial: 6.1 (±1) final: 4.9 (±1) |
| Depression score associated with neuropathic (presumed pain component) | initial: 2 to 20 final: <90% of initial value | initial: 2 to 20 final: <75% of initial value | initial: 5 to 12 final: 3 to 10 | initial: 7 to 10 final: 5 to 8 | initial: 8.8 (±1) final: 6.2 (±1) |
| Depression score associated with neuropathic (defined) | initial: 2 to 20 final: <90% of initial value | initial: 2 to 20 final: <75% of initial value | initial: 5 to 12 final: 2 to 9 | initial: 7 to 10 final: 4 to 7 | initial: 8.3 (±1) final: 5.8 (±1) |

Preferably, the time period between the determination of the initial and the final depression score is 6 months, more preferably 3 months, still more preferably 30 days, yet more preferably 20 days, most preferably 10 days. Furthermore, the daily dosage of tapentadol is preferably within the range of from 25 to 600 mg, more preferably from 50 to 300 mg, most preferably from 50 to 150 mg.

In another preferred embodiment, tapentadol is used in the treatment of depression and/or anxiety, wherein the depression and anxiety scores are reduced. The reduction of the mean values for the anxiety scores due to the administration of tapentadol over the time periods of 10, 20 and 30 days are summarized as preferred embodiments E31 to E35 below. Each %-value indicates the remaining mean anxiety score after the defined time period relative to the initial mean anxiety score.

| Time | E31 | E32 | E33 | E34 | E35 |
|---|---|---|---|---|---|
| 10 days | <99% | <95% | <90% | <80% | <75% |
| 20 days | <95% | <90% | <85% | <60% | <50% |
| 30 days | <92% | <85% | <80% | <50% | <20% |

Preferably, the daily dosage of tapentadol is within the range of from 25 to 600 mg, preferably from 50 to 300 mg, more preferably from 50 to 150 mg.

The reduction of the mean values for the depression scores due to the administration of tapentadol over the time periods of 10, 20 and 30 days are summarized as preferred embodiments E36 to E30 below. Each %-value indicates the remaining mean depression score after the defined time period relative to the initial mean depression score.

| Time | E36 | E37 | E38 | E39 | E40 |
|---|---|---|---|---|---|
| 10 days | <99% | <95% | <90% | <80% | <75% |
| 20 days | <95% | <90% | <85% | <60% | <50% |
| 30 days | <92% | <85% | <80% | <50% | <20% |

Preferably, the daily dosage of tapentadol is within the range of from 25 to 600 mg, preferably from 50 to 300 mg, more preferably from 50 to 150 mg.

Preferably, tapentadol is administered in form of a pharmaceutical composition comprising tapentadol and at least one pharmaceutically acceptable additive and/or auxiliary substance.

Suitable pharmaceutically acceptable additives and/or auxiliary substances in the context of this invention include all the substances known to the expert from the prior art for realizing galenical formulations. The choice of these auxiliary substances and the amounts thereof to be employed depend on whether the administration unit/dosage form is to be administered orally, intravenously, intraperitoneally, intradermally, intramuscularly, intranasally, buccally or locally. Formulations in the form of tablets, chewable tablets, coated tablets, capsules, granules, drops, juices or syrups are suitable for oral administration, and solutions, suspensions, easily reconstitutable dry formulations and sprays are suitable for parenteral, topical and inhalatory administration. Suppositories for use in the rectum are a further possibility. The use in a depot in dissolved form, a carrier film or a patch, optionally with the addition of agents which promote penetration through the skin, are examples of suitable forms for percutaneous administration.

Examples of pharmaceutically acceptable auxiliary substances and additives for orally administrable units or dosage forms include disintegrating agents, lubricants, binders, fillers, mold release agents, optionally solvents, flavorings, sugars, in particular carrier agents, diluents, dyestuffs, antioxidants etc. For suppositories, inter alia, waxes and fatty acid esters can be used, and for compositions for parental administration carrier substances, preservatives, suspension auxiliaries etc. can be used.

The dosage forms comprise preferably 0.05 wt.-% to 99.5 wt.-% of tapentadol, more preferably 0.1 to 90 wt.-%, still more preferably 0.5 to 80 wt.-%, most preferably 1.0 to 50 wt.-% and in particular 5.0 to 20 wt.-%.

Suitable pharmaceutically acceptable auxiliary substances include, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethyl cellulose, cellulose acetate, shellac, cetyl alcohol, polyvinylpyrrolidone, paraffins, waxes, naturally occurring and synthetic gums, gum acacia, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and polypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The administration units/dosage forms according to the invention may be controlled release, delayed release, prolonged release/extended release, sustained release, repeat-action release, etc. Prolonged release administration units/dosage forms are preferred.

The administration units/dosage forms according to the invention are prepared with the aid of means, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

Thus, e.g., for a solid formulation, such as a tablet, tapentadol can be granulated with a pharmaceutical carrier, e.g. conventional tablet constituents, such as maize starch, lactose, sucrose, sorbitol, talc, magnesium stearate, dicalcium phosphate or physiologically acceptable gums, and pharmaceutical diluents, such as e.g. water, in order to form a solid composition which comprises tapentadol in homogeneous distribution. Homogeneous distribution is understood here as meaning that tapentadol is uniformly distributed over the entire composition, so that this can easily be divided into unit dose forms, such as tablets, pills or capsules, having the same activity. The solid composition is then divided into unit dose forms. The administration units according to the invention can also be coated or compounded in another manner in order to provide a dose form with delayed release. Suitable coating compositions are, inter alia, polymeric acids and mixtures of polymeric acids with materials such as e.g. shellac, cetyl alcohol and/or cellulose acetate.

Tapentadol can be released in a delayed or prolonged or sustained manner from administration units/dosage forms which can be used orally, rectally or percutaneously. Corresponding formulations, in particular in the form of a "twice daily (bid)" preparation which has to be taken only twice a day (bid), are particularly preferred for the indication according to the invention (cf. US-A-2005-58706).

Delayed or prolonged or sustained release of tapentadol may be achieved by administration units/dosage forms which contain tapentadol in a matrix, which contains e.g. 1 to 80% by weight, in particular 5 to 80 by weight, of one or more hydrophilic or hydrophobic polymers as physiologically acceptable matrix forming agents and which comprise cellulose ethers and/or cellulose esters having a viscosity (determined using a Pharm. Eu. capillary viscosimeter) of 3,000 to 150,000 mPa s in a 2% by weight aqueous solution at 20° C. as physiologically acceptable matrix forming agents. Preferred physiologically acceptable matrix forming agents include polyethylene oxide having a molecular mass of more than 0.5 mio g/mol, cellulose ethers and/or cellulose esters having a viscosity between 10,000, in particular 50,000 mPa s, and 150,000 mPa s in a 2% by weight aqueous solution at 20° C. Particularly suitable physiologically acceptable matrix forming agents may be selected from the group consisting of hydroxypropylmethyl celluloses (HPMC), hydroxyethyl celluloses, hydroxypropyl celluloses (HPC), methyl celluloses, ethyl celluloses and carboxymethyl celluloses and are selected, in particular, from the group consisting of HPMCs, hydroxyethyl celluloses and HPCs. HPMCs having a viscosity of approximately 100,000 mPa s, measured in a 2% by weight aqueous solution at 20° C. are most preferred.

The administration units/dosage forms according to the invention can exist both as a simple tablet and as a coated tablet, for example as a film tablet or dragee. The tablets are typically round and biconvex, but oblong tablet shapes which allow the tablet to be divided are also possible. Granules, spheroids, pellets or microcapsules which are poured into sachets or capsules or may be compressed to disintegrating tablets are also possible within the scope of the invention.

Instead of a slow release matrix, it is also possible to use a normal release matrix with a coating which retards release of the pharmacologically active ingredient. For example, tapentadol can be contained in a conventional matrix of microcrystalline cellulose and optionally further pharmaceutical auxiliaries such as binders, fillers, glidants, lubricants and flow regulators, which are covered or coated with a material controlling the slow release of tapentadol in an aqueous medium. Suitable coating agents include, for example, water-insoluble waxes and polymers such as polymethacrylates (Eudragit or the like) or water-insoluble celluloses, in particular ethyl cellulose. The coating material can optionally also contain water-soluble polymers such as polyvinyl pyrrolidone, water-soluble celluloses such as hydroxypropylmethyl cellulose or hydroxypropyl cellulose, other water-soluble agents such as Polysorbate 80 or hydrophilic pore-forming agents such as polyethylene glycol, lactose or mannitol.

As an alternative or a supplement to the possibilities of a slow release matrix in the delayed release or prolonged release or sustained release dosage forms or of a normal release matrix with a coating which retards the release of tapentadol, an osmotically driven release system can also be used to achieve a slow release. Embodiments and examples of the actual production of osmotically driven release systems can be found in U.S. Pat. Nos. 4,765,989, 4,783,337, and 4,612,008.

The following examples further illustrate the invention but are not to be construed as limiting its scope.

EXAMPLE

Aim and Design

The effectiveness of tapentadol hydrochloride PR and tapentadol hydrochloride IR in the treatment of pain in a subject suffering from depression and/or from anxiety, and in the treatment of depression and/or of anxiety has been demonstrated in a clinical study in subjects with severe and chronic nociceptive, mixed with neuropathic low back pain. A subgroup suffering from neuropathic pain due to lumbar radiculopathy was also investigated.

This was a multicenter, multinational, open-label, effectiveness phase IIIb trial to evaluate effectiveness and safety of tapentadol prolonged release treatment in patients with inadequately managed, severe chronic low back pain with or without a neuropathic pain component. Patients taking WHO Step II analgesics discontinued those analgesics before starting study medication; patients taking Step I analgesics and/or centrally acting co-analgesics continued on the same dose. Patients who enrolled in the study and were taking WHO Step I or II analgesics had an average pain intensity score of >5 on an 11-point NRS-3 (average pain over 3 days prior to assessment) at screening; patients who were taking no regular analgesic treatment had an average pain intensity score (NRS-3) of >6. All patients received tapentadol prolonged release (50-250 mg bid) for up to 12 weeks (5-week titration period and a 7-week maintenance period). Tapentadol immediate release (IR) 50 mg (twice a day, hours apart) was permitted (combined total daily dose of tapentadol prolonged release and tapentadol IR, 500 mg/day). The primary efficacy endpoint was the change from Baseline to Week 6 (when tapentadol prolonged release doses were stable) in average pain intensity on the 11-point NRS-3 using the last observation carried forward (LOCF) for imputing missing scores. The painDETECT questionnaire was used to evaluate the likelihood of a neuropathic pain component of low back pain; patients were classified as painDETECT "negative," "unclear," or "positive." The population of patients classified as painDETECT negative was limited to approximately 30% of the total population.

In the painDETECT positive trial population the "diagnosis of lumbar radiculopathy" was evaluated which was defined per study protocol according following criteria:
  typical dermatomal pain (radiating beyond the knee towards the foot, pain evoked by stretching within distribution of the ischiadic/femoral nerve)
  signs of root dysfunction:
  such as sensory impairment, motor symptoms from compression of lumbar nerve root (L4, L5, S1).
  and/or absent or diminished quadriceps femoris or triceps surae reflexes.
  and/or quantitative sensory testing (QST) deficit and pain distribution present in the same dermatomal area.

In subjects with neuropathic pain further characterization of the symptoms was performed. These additional assessments referred explicitly to the neuropathic component of the LBP (Neuropathic Pain Symptom Inventory (NPSI), Short Form McGill Pain Questionnaire (SF-MPQ).NRS-3 for pain radiating towards or into the leg).

All subjects completed Short Form-36 (SF-36) and EuroQol-5 Dimension (EQ-5D) questionnaires and the Hospital Anxiety and Depression Scale (HADS). The Patient Global Impression of Change (PGIC) and Clinical global impression of change (CGIC) were also used as secondary endpoints. For both tests, patients completed the statement, "since I began trial treatment, I would rate my overall condition as," using 7 possible responses ("very much worse" to "very much improved"). Adverse events were recorded throughout the trial. Furthermore, 51.8% of the painDETECT positive trial population had a "diagnosis of lumbar radiculopathy" as defined per study protocol.

Results

Short Form 36® Health Survey (SF-36®) scores: SF-36 physical functioning, bodily pain, general health, role-emotional and physical component summary scores improved from Baseline to Week 12 for patients who were painDETECT negative or unclear/positive (all P<0.05); for those who were unclear/positive, role-physical, vitality, social functioning, mental health, reported health transition and mental component summary scores also improved (all P<0.05).

EuroQol-5 Dimension (EQ-5D) scores: the mean (SD) change from Baseline to Week 12 in the EQ-5D health status index score was 0.18 (0.25; P=0.0022) for patients who were painDETECT negative and 0.36 (0.32); P<0.0001) for those positive.

Hospital Anxiety and Depression Scale (HADS): Baseline mean (SD) HADS depression (6.5[3.96] vs. 8.5[4.27]) and anxiety (6.2[4.10] vs. 8.4[4.26]) scores were lower for patients with a painDETECT negative vs. an unclear/positive result, respectively. HADS depression and anxiety scores improved steadily from Baseline to Week 12 for patients who were painDETECT unclear/positive (P<0.0001 at Visit 12 for depression and anxiety), but not significantly for those with a negative result. HADS depression and anxiety scores improved steadily from Baseline to Week 12 for patients with positive diagnosis of lumbar radiculopathy-neuropathic pain subset (0.0023 at Visit 12 for depression, p=0.0105 at Visit 12 for anxiety).

Patient Global Impression of Change: The percentage of patients reporting a rating of "very much improved" or "much improved" on the PGIC increased from 15.1% (26/172) at Week 1 to 48.6% (67/138) at Week 6 and 67.1% (61/91) at Week 12.

Clinical global impression of change (CGIC): The percentage of patients reporting a rating of "very much improved" or "much improved" on the CGIC increased from 15.1% (26/172) at Week 1 to 50.7% (70/138) at Week 6 and 68.2% (62/91) at Week 12.

Subject satisfaction with previous/new treatment: The percentage of patients reporting a rating of "excellent" or "very good" increased from 0.0% (0/175) at Baseline to 29.7% (41/138) at Week 6 and 52.8% (48/91) at Week 12.

In the following
(i) N is the number of subjects of the specified diagnosis group,
(ii) n is the number of subjects with data available,
(iii) "Mean" is the mean score of the subjects, i.e. the sum of all scores is divided by the number of subjects,
(iv) SD is the standard deviation,
(v) "Median" is the median score of the subjects, i.e. the middle score in the set of scores,
(vi) "Range" is the range of scores of the subjects, i.e. the range defined by the lowest and the highest score of the set of scores.

First, the depression scores are presented. The total number of subjects in the clinical study: N=175

| Depression score | n | Mean (SD) | Median | Range |
| --- | --- | --- | --- | --- |
| Screening | 174 | 7.9 (4.37) | 8.0 | 1-20 |
| Baseline | 173 | 7.9 (4.27) | 8.0 | 0-21 |
| Visit 1 | 164 | 7.8 (4.47) | 7.0 | 0-20 |
| Visit 5 | 141 | 6.9 (4.26) | 6.0 | 0-18 |
| Visit 6 | 130 | 6.6 (4.41) | 6.0 | 0-19 |
| Visit 7 | 127 | 6.1 (4.40) | 6.0 | 0-18 |
| Visit 8 | 119 | 6.2 (4.16) | 6.0 | 0-17 |
| Visit 9 | 87 | 6.1 (4.48) | 6.0 | 0-17 |
| Visit 10 | 85 | 6.2 (4.66) | 6.0 | 0-21 |
| Visit 11 | 85 | 5.9 (4.59) | 5.0 | 0-17 |
| Visit 12 | 89 | 5.7 (4.35) | 5.0 | 0-18 |

Total number of subjects with nociceptive pain: N=49

| Depression score | n | Mean (SD) | Median | Range |
| --- | --- | --- | --- | --- |
| Screening | 48 | 6.8 (4.17) | 6.0 | 1-16 |
| Baseline | 49 | 6.5 (3.96) | 6.0 | 0-15 |
| Visit 1 | 43 | 6.1 (3.90) | 5.0 | 0-15 |
| Visit 5 | 37 | 5.6 (3.68) | 5.0 | 0-13 |
| Visit 6 | 34 | 5.3 (4.03) | 4.0 | 1-15 |
| Visit 7 | 35 | 5.0 (3.63) | 4.0 | 1-14 |
| Visit 8 | 32 | 5.5 (3.90) | 4.5 | 0-16 |
| Visit 9 | 25 | 5.4 (3.49) | 5.0 | 1-12 |
| Visit 10 | 24 | 5.5 (3.34) | 5.5 | 1-12 |
| Visit 11 | 23 | 5.6 (4.04) | 5.0 | 0-14 |
| Visit 12 | 23 | 4.9 (3.13) | 4.0 | 0-11 |

Total number of subjects with presumed neuropathic pain component: N=41

| Depression score | n | Mean (SD) | Median | Range |
| --- | --- | --- | --- | --- |
| Screening | 41 | 7.4 (3.69) | 7.0 | 1-17 |
| Baseline | 40 | 7.9 (3.84) | 7.5 | 1-17 |
| Visit 1 | 38 | 8.8 (4.59) | 8.5 | 1-18 |
| Visit 5 | 33 | 7.5 (4.59) | 7.0 | 0-18 |
| Visit 6 | 30 | 7.5 (4.60) | 7.5 | 0-17 |
| Visit 7 | 32 | 7.0 (4.71) | 6.5 | 0-18 |
| Visit 8 | 28 | 6.4 (4.24) | 6.0 | 1-14 |
| Visit 9 | 19 | 6.4 (4.32) | 6.0 | 0-15 |
| Visit 10 | 19 | 6.4 (5.34) | 5.0 | 0-21 |
| Visit 11 | 20 | 6.4 (5.11) | 5.0 | 0-17 |
| Visit 12 | 21 | 6.2 (4.66) | 5.0 | 0-17 |

Total number of subjects with defined neuropathic pain: N=85

| Depression score | n | Mean (SD) | Median | Range |
| --- | --- | --- | --- | --- |
| Screening | 85 | 8.9 (4.63) | 9.0 | 1-20 |
| Baseline | 84 | 8.7 (4.46) | 8.5 | 0-21 |
| Visit 1 | 83 | 8.3 (4.51) | 8.0 | 1-20 |
| Visit 5 | 71 | 7.3 (4.29) | 7.0 | 1-17 |
| Visit 6 | 66 | 6.8 (4.41) | 6.0 | 0-19 |
| Visit 7 | 60 | 6.2 (4.56) | 6.0 | 0-16 |
| Visit 8 | 59 | 6.4 (4.28) | 6.0 | 1-17 |
| Visit 9 | 43 | 6.5 (5.06) | 6.0 | 0-17 |
| Visit 10 | 42 | 6.5 (5.04) | 6.0 | 0-19 |
| Visit 11 | 42 | 5.9 (4.70) | 5.5 | 0-15 |
| Visit 12 | 45 | 5.8 (4.76) | 5.0 | 0-18 |

Total number of subjects with presumed or defined neuropathic pain component: N=126

| Depression score | n | Mean (SD) | Median | Range |
| --- | --- | --- | --- | --- |
| Screening | 126 | 8.4 (4.38) | 8.0 | 1-20 |
| Baseline | 124 | 8.5 (4.27) | 8.0 | 0-21 |
| Visit 1 | 121 | 8.5 (4.52) | 8.0 | 1-20 |
| Visit 5 | 104 | 7.4 (4.37) | 7.0 | 0-18 |
| Visit 6 | 96 | 7.1 (4.46) | 7.0 | 0-19 |
| Visit 7 | 92 | 6.5 (4.61) | 6.0 | 0-18 |
| Visit 8 | 87 | 6.4 (4.24) | 6.0 | 1-17 |
| Visit 9 | 62 | 6.5 (4.81) | 6.0 | 0-17 |
| Visit 10 | 61 | 6.5 (5.09) | 6.0 | 0-21 |
| Visit 11 | 62 | 6.0 (4.80) | 5.0 | 0-17 |
| Visit 12 | 66 | 5.9 (4.70) | 5.0 | 0-18 |

Total number of subjects with positive diagnosis of lumbar radiculopathy-neuropathic pain subset: N=44

| Depression score | n | Mean (SD) | Median | Range |
| --- | --- | --- | --- | --- |
| Screening | 44 | 8.5 (4.70) | 8.5 | 2-20 |
| Baseline | 44 | 8.2 (4.09) | 8.0 | 0-17 |
| Visit 1 | 44 | 7.5 (3.69) | 7.5 | 1-15 |
| Visit 5 | 40 | 6.7 (3.77) | 6.0 | 1-14 |
| Visit 6 | 38 | 6.3 (3.67) | 6.0 | 1-13 |
| Visit 7 | 34 | 5.4 (3.85) | 5.0 | 0-14 |
| Visit 8 | 35 | 5.8 (3.71) | 6.0 | 1-14 |
| Visit 9 | 24 | 6.2 (4.63) | 7.5 | 1-14 |
| Visit 10 | 25 | 6.2 (4.50) | 7.0 | 0-13 |
| Visit 11 | 26 | 6.0 (4.69) | 6.5 | 0-14 |
| Visit 12 | 27 | 5.3 (4.09) | 5.0 | 0-12 |

Second, the anxiety scores are presented. The total number of subjects: N=175

| Anxiety score | n | Mean (SD) | Median | Range |
| --- | --- | --- | --- | --- |
| Screening | 174 | 8.1 (3.99) | 8.0 | 1-19 |
| Baseline | 173 | 7.8 (4.32) | 7.0 | 0-18 |
| Visit 1 | 164 | 7.6 (4.28) | 7.0 | 0-18 |
| Visit 5 | 141 | 6.8 (3.94) | 7.0 | 0-17 |
| Visit 6 | 130 | 6.6 (4.02) | 6.0 | 0-18 |
| Visit 7 | 127 | 5.9 (3.99) | 6.0 | 0-18 |
| Visit 8 | 119 | 5.6 (3.95) | 5.0 | 0-18 |
| Visit 9 | 87 | 5.7 (4.10) | 4.0 | 0-19 |
| Visit 10 | 85 | 5.6 (4.16) | 5.0 | 0-19 |
| Visit 11 | 85 | 5.4 (3.91) | 5.0 | 0-14 |
| Visit 12 | 89 | 5.2 (3.73) | 4.0 | 0-13 |

Total number of subjects with nociceptive pain: N=49

| Anxiety score | n | Mean (SD) | Median | Range |
| --- | --- | --- | --- | --- |
| Screening | 48 | 6.7 (3.80) | 6.5 | 1-15 |
| Baseline | 49 | 6.2 (4.10) | 5.0 | 0-16 |
| Visit 1 | 43 | 5.9 (4.19) | 6.0 | 0-18 |
| Visit 5 | 37 | 6.1 (3.80) | 5.0 | 0-14 |
| Visit 6 | 34 | 5.8 (4.68) | 5.0 | 0-18 |
| Visit 7 | 35 | 5.6 (4.15) | 5.0 | 0-18 |
| Visit 8 | 32 | 5.4 (4.40) | 4.0 | 0-18 |
| Visit 9 | 25 | 4.6 (3.34) | 4.0 | 0-13 |
| Visit 10 | 24 | 4.7 (3.21) | 4.0 | 0-11 |
| Visit 11 | 23 | 4.8 (3.77) | 4.0 | 0-14 |
| Visit 12 | 23 | 4.5 (3.65) | 3.0 | 0-13 |

Total number of subjects with presumed neuropathic pain component: N=41

| Anxiety score | n | Mean (SD) | Median | Range |
| --- | --- | --- | --- | --- |
| Screening | 41 | 8.3 (3.68) | 8.0 | 1-17 |
| Baseline | 40 | 8.3 (4.15) | 7.0 | 2-17 |
| Visit 1 | 38 | 7.9 (4.52) | 7.0 | 2-17 |
| Visit 5 | 33 | 6.7 (4.22) | 7.0 | 0-15 |
| Visit 6 | 30 | 6.9 (3.99) | 6.0 | 1-16 |
| Visit 7 | 32 | 5.9 (4.08) | 5.5 | 0-13 |
| Visit 8 | 28 | 4.9 (4.04) | 4.0 | 0-14 |
| Visit 9 | 19 | 6.1 (5.10) | 6.0 | 0-19 |
| Visit 10 | 19 | 5.5 (5.46) | 4.0 | 0-19 |
| Visit 11 | 20 | 5.1 (4.25) | 4.0 | 0-13 |
| Visit 12 | 21 | 4.8 (3.67) | 4.0 | 0-12 |

Total number of subjects with defined neuropathic pain: N=85

| Anxiety score | n | Mean (SD) | Median | Range |
| --- | --- | --- | --- | --- |
| Screening | 85 | 8.9 (4.07) | 9.0 | 1-19 |
| Baseline | 84 | 8.5 (4.33) | 8.5 | 0-18 |
| Visit 1 | 83 | 8.3 (4.01) | 8.0 | 0-18 |
| Visit 5 | 71 | 7.2 (3.89) | 8.0 | 0-17 |
| Visit 6 | 66 | 6.9 (3.66) | 6.0 | 0-16 |
| Visit 7 | 60 | 6.1 (3.91) | 6.0 | 0-16 |
| Visit 8 | 59 | 6.0 (3.66) | 5.0 | 0-14 |
| Visit 9 | 43 | 6.1 (3.99) | 5.0 | 1-16 |
| Visit 10 | 42 | 6.1 (3.98) | 6.0 | 0-16 |
| Visit 11 | 42 | 5.9 (3.84) | 5.5 | 0-13 |
| Visit 12 | 45 | 5.7 (3.80) | 5.0 | 0-13 |

Total number of subjects with presumed or defined neuropathic pain component: N=126

| Anxiety score | n | Mean (SD) | Median | Range |
|---|---|---|---|---|
| Screening | 126 | 8.7 (3.94) | 9.0 | 1-19 |
| Baseline | 124 | 8.4 (4.26) | 8.0 | 0-18 |
| Visit 1 | 121 | 8.2 (4.16) | 8.0 | 0-18 |
| Visit 5 | 104 | 7.0 (3.98) | 7.0 | 0-17 |
| Visit 6 | 96 | 6.9 (3.75) | 6.0 | 0-16 |
| Visit 7 | 92 | 6.0 (3.95) | 6.0 | 0-16 |
| Visit 8 | 87 | 5.7 (3.80) | 5.0 | 0-14 |
| Visit 9 | 62 | 6.1 (4.32) | 5.0 | 0-19 |
| Visit 10 | 61 | 5.9 (4.46) | 5.0 | 0-19 |
| Visit 11 | 62 | 5.6 (3.96) | 5.0 | 0-13 |
| Visit 12 | 66 | 5.4 (3.76) | 5.0 | 0-13 |

Total number of subjects with positive diagnosis of lumbar radiculopathy-neuropathic pain subset: N=44

| Anxiety score | N | Mean (SD) | Median | Range |
|---|---|---|---|---|
| Screening | 44 | 8.9 (4.06) | 9.0 | 1-17 |
| Baseline | 44 | 8.6 (4.23) | 9.0 | 0-18 |
| Visit 1 | 44 | 8.7 (3.64) | 9.0 | 1-18 |
| Visit 5 | 40 | 6.8 (3.39) | 7.5 | 1-15 |
| Visit 6 | 38 | 7.1 (3.46) | 7.5 | 1-13 |
| Visit 7 | 34 | 6.1 (3.85) | 6.0 | 0-15 |
| Visit 8 | 35 | 5.9 (3.74) | 5.0 | 0-13 |
| Visit 9 | 24 | 6.2 (4.01) | 5.0 | 1-13 |
| Visit 10 | 25 | 6.1 (3.85) | 6.0 | 0-13 |
| Visit 11 | 26 | 6.3 (4.25) | 6.5 | 0-13 |
| Visit 12 | 27 | 5.7 (3.59) | 6.0 | 0-11 |

The foregoing clinical data clearly demonstrate that tapentadol exhibits a significant efficacy against depression and anxiety.

The changes from baseline at visits 6, 8 and 12 are summarized in the following tables:

Depression:

|  | nociceptive | presumed neuropathic | defined neuropathic | lumbar radiculopathy | presumed or defined neuropathic | total |
|---|---|---|---|---|---|---|
| Visit 6 | | | | | | |
| n | 34 | 29 | 65 | 38 | 94 | 128 |
| Mean (SD) | −1.0 (3.15) | −0.4 (3.55) | −1.7 (3.43) | −1.7 (3.23) | −1.3 (3.50) | −1.2 (3.40) |
| Median | −1.0 | −0.0 | −2.0 | −1.0 | −1.0 | −1.0 |
| Min, Max | −11, 5 | −12, 4 | −10, 8 | −9, 4 | −12, 8 | −12, 8 |
| 95% CI | [−2.1; 0.1] | [−1.8; 0.9] | [−2.6; −0.9] | [−2.7; −0.6] | [−2.0; −0.6] | [−1.8; −0.6] |
| p-value# | 0.0813 | 0.5354 | 0.0002 | 0.0027 | <0.0005 | <0.0001 |
| Visit 8 | | | | | | |
| n | 32 | 27 | 58 | 35 | 85 | 117 |
| Mean (SD) | −0.8 (2.31) | −1.0 (3.13) | −2.3 (3.33) | −2.1 (3.54) | −1.9 (3.30) | −1.6 (3.09) |
| Median | −1.0 | −1.0 | −1.5 | −1.0 | −1.0 | −1.0 |
| Min, Max | −8, 4 | −12, 3 | −12, 3 | −10, 3 | −12, 3 | −12, 4 |
| 95% CI | [−1.6; 0.0] | [−2.2; 0.2] | [−3.2; −1.4] | [−3.3; −0.9] | [−2.6; −1.2] | [−2.1; −1.0] |
| p-value# | 0.0551 | <0.1084 | <0.0001 | 0.0014 | <0.0001 | <0.0001 |
| Visit 12 | | | | | | |
| n | 23 | 21 | 45 | 27 | 66 | 89 |
| Mean (SD) | −0.5 (2.86) | −1.5 (3.30) | −2.2 (3.31) | −2.1 (3.30) | −2.0 (3.30) | −1.6 (3.24) |
| Median | 0.0 | −2.0 | −2.0 | −1.0 | −2.0 | −2.0 |
| Min, Max | −5, 4 | −10, 6 | −9, 6 | −9, 3 | −10, 6 | −10, 6 |
| 95% CI | [−1.7; 0.8] | [−3.0; 0.0] | [−3.2; −1.2] | [−3.5; −0.8] | [−2.8; −1.2] | [−2.3; −0.9] |
| p-value# | 0.4309 | 0.0534 | 0.0001 | 0.0023 | <0.0001 | <0.0001 |

Anxiety:

|  | nociceptive | presumed neuropathic | defined neuropathic | lumbar radiculopathy | presumed or defined neuropathic | total |
|---|---|---|---|---|---|---|
| Visit 6 | | | | | | |
| n | 34 | 29 | 65 | 38 | 94 | 128 |
| Mean (SD) | −0.3 (2.93) | −1.6 (3.58) | −1.4 (3.44) | −1.4 (3.88) | −1.5 (3.47) | −1.2 (3.36) |
| Median | 0.0 | −1.0 | −1.0 | −0.5 | −1.0 | −1.0 |
| Min, Max | −7, 5 | −9, 9 | −10, 5 | −10, 5 | −10, 9 | −10, 9 |
| 95% CI | [−1.3; 0.7] | [−2.9; −0.2] | [−2.3; −0.6] | [−2.6; −0.1] | [−2.2; −0.7] | [−1.7; −0.6] |
| p-value# | 0.5242 | 0.0271 | 0.0015 | 0.0361 | <0.0001 | 0.0002 |
| Visit 8 | | | | | | |
| n | 32 | 27 | 58 | 35 | 85 | 117 |
| Mean (SD) | −0.7 (3.88) | −2.9 (3.11) | −2.2 (3.77) | −2.4 (4.23) | −2.4 (3.57) | −1.9 (3.72) |
| Median | −1.0 | −2.0 | −2.0 | −1.0 | −2.0 | −2.0 |
| Min, Max | −7, 14 | −11, 2 | −13, 5 | −13, 5 | −13, 5 | −13, 14 |
| 95% CI | [−2.1; 0.7] | [−4.1; −1.7] | [−3.2; −1.2] | [−3.9; −1.0] | [−3.2; −1.6] | [−2.6; −1.3] |
| p-value# | 0.3027 | <0.0001 | <0.0001 | 0.0018 | <0.0001 | <0.0001 |

-continued

|  | nociceptive | presumed neuropathic | defined neuropathic | lumbar radiculopathy | presumed or defined neuropathic | total |
| --- | --- | --- | --- | --- | --- | --- |
| Visit 12 | | | | | | |
| n | 23 | 21 | 45 | 27 | 66 | 89 |
| Mean (SD) | −0.8 (2.82) | −3.1 (3.16) | −2.3 (4.14) | −2.2 (4.11) | −2.5 (3.85) | −2.1 (3.67) |
| Median | −1.0 | −3.0 | −2.0 | −2.0 | −2.0 | −2.0 |
| Min, Max | −9, 4 | −13, 0 | −11, 6 | −10, 4 | −13, 6 | −13, 6 |
| 95% CI | [−2.0; 0.4] | [−4.5; −1.7] | [−3.5; −1.0] | [−3.8; −0.6] | [−3.5; −1.6] | [−2.9; −1.3] |
| p-value# | 0.1744 | 0.0002 | 0.0006 | 0.0105 | <0.0001 | <0.0001 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method of treating or inhibiting depression and/or anxiety in a subject in need thereof, said method comprising administering to the subject a therapeutically effective amount of tapentadol as the only pharmacologically active ingredient, wherein the subject suffers from depression and/or anxiety.

2. The method of claim 1, wherein the depression and/or anxiety induces psychogenic pain.

3. The method according to claim 1, wherein the depression and/or anxiety induces one or more symptoms selected from the group consisting of depressed affect, generalized anxiety, panic attacks, insomnia, suicidal thoughts, social inhibition, loss of energy, hopelessness, anhedonia, mood disturbances, irritability, disability, gastrointestinal disturbances, skin reactions, back pain, chest pain, headache, muscle pain and non-specific pains and aches.

4. The method of claim 1, wherein the tapentadol is used for
 a) treating or inhibiting depression in a subject suffering from depression and pain; or
 b) treating or inhibiting anxiety in a subject suffering from anxiety and pain.

5. The method of claim 1, wherein the tapentadol is administered orally.

6. The method of claim 1, wherein the tapentadol is administered once daily or twice daily.

7. The method of claim 1, wherein the tapentadol is administered at a daily dose within the range of from 25 to 600 mg.

8. The method of claim 1, wherein the subject further suffers from moderate or severe pain.

9. The method of claim 1, wherein the subject further suffers from chronic pain.

10. The method of claim 9, wherein the chronic pain is pain selected from the group consisting of cancer pain, chemotherapy-induced pain, upper back pain, low back pain, inflammatory pain including pain associated with rheumatic diseases, arthritic pain, ankylosing spondylitis, myofascial pain, pain associated with musculo-skeletal disorders, muscle pain, skeletal pain, joint pain, chronic pain associated with fibromyalgia, pain from strains or sprains, persistent post-operative pain, persistent posttraumatic pain, renal colic, irritable bowel syndrome-related pain, gastrointestinal pain, pelvic pain, abdominal pain, ischemic pain, angina pain, pain associated with claudication, pain accompanying myocardial infarction, vascular pain, central nervous system trauma, facial pain, migraine-related pain, headache-related pain, orofacial pain, persistent pain deriving from damaged or inflamed somatic tissue, and combinations of two or more of the foregoing.

11. The method of claim 1, wherein the subject further suffers from pain selected from the group consisting of neuropathic pain, nociceptive pain, psychogenic pain, phantom pain and combinations of two or more of the foregoing.

12. The method of claim 11, wherein the pain is neuropathic pain.

13. The method according to claim 12, wherein the neuropathic pain is selected from the group consisting of diabetic neuralgia, monoradiculopathies, trigeminal neuralgia, post-herpetic neuralgia persistent postoperative or post-traumatic pain, hyperalgia, allodynia, fibromyalgia, complex regional pain syndrome, pain associated with multiple sclerosis, AIDS-related neuropathy, thalamic pain, paraplegic pain caused by myelopathy, anesthesia dolorosa, low back pain, reflex sympathetic dystrophy/causalgia, cancer pain, chemotherapy-induced pain, post-thoracotomy pain, entrapment neuropathy, and peripheral neuropathy.

* * * * *